(12) United States Patent
Harmalker et al.

(10) Patent No.: US 8,703,160 B2
(45) Date of Patent: Apr. 22, 2014

(54) MOISTURIZING COMPOSITIONS

(75) Inventors: Subhash Harmalker, Somerset, NJ (US); Kathryn Ash, Morris Plains, NJ (US)

(73) Assignee: Colgate-Palmolive Company, New York, NY (US)

( * ) Notice: Subject to any disclaimer, the term of this patent is extended or adjusted under 35 U.S.C. 154(b) by 2099 days.

(21) Appl. No.: 11/466,940

(22) Filed: Aug. 24, 2006

(65) Prior Publication Data

US 2007/0048235 A1 Mar. 1, 2007

Related U.S. Application Data

(60) Provisional application No. 60/711,121, filed on Aug. 25, 2005.

(51) Int. Cl.
*A61K 8/02* (2006.01)

(52) U.S. Cl.
USPC .......................................................... 424/401

(58) Field of Classification Search
USPC .......................................................... 424/401
See application file for complete search history.

(56) References Cited

U.S. PATENT DOCUMENTS

| | | | |
|---|---|---|---|
| 2,589,674 A | 3/1952 | Cook et al. | |
| 2,678,934 A | 5/1954 | Grummitt et al. | |
| 4,740,367 A | 4/1988 | Force et al. | |
| 5,439,682 A | 8/1995 | Wivell et al. | |
| 5,599,549 A | 2/1997 | Wivell et al. | |
| 5,723,110 A | 3/1998 | Yamamoto et al. | |
| 5,883,059 A | 3/1999 | Furman et al. | |
| 5,942,479 A | 8/1999 | Frankenbach et al. | |
| 5,977,037 A | 11/1999 | Giret et al. | |
| 6,113,892 A * | 9/2000 | Newell et al. | 424/70.19 |
| 6,225,485 B1 | 5/2001 | Bertz et al. | |
| 6,242,491 B1 | 6/2001 | Kaddurah-Daouk | |
| 6,248,703 B1 | 6/2001 | Finucane et al. | |
| 6,265,364 B1 | 7/2001 | Kilpatrick-Liverman et al. | |
| 6,475,965 B2 | 11/2002 | Kilpatrick-Liverman et al. | |
| 6,780,825 B2 | 8/2004 | Piterski et al. | |
| 6,869,977 B1 | 3/2005 | O'Lenick, Jr. et al. | |
| 7,361,710 B2 * | 4/2008 | Thames et al. | 524/785 |
| 2001/0014316 A1 | 8/2001 | Harbeck | |
| 2001/0050507 A1 | 12/2001 | Boucherie | |
| 2004/0253282 A1 | 12/2004 | Sauermann et al. | |
| 2004/0258717 A1 | 12/2004 | Sauermann et al. | |
| 2005/0113268 A1 | 5/2005 | Landa et al. | |
| 2005/0113269 A1 | 5/2005 | Landa et al. | |
| 2006/0088495 A1 | 4/2006 | Harichian et al. | |
| 2006/0088496 A1 | 4/2006 | McManus et al. | |
| 2006/0089277 A1 | 4/2006 | Harding et al. | |
| 2006/0089290 A1 | 4/2006 | McManus et al. | |
| 2006/0272113 A1 | 12/2006 | Cato et al. | |
| 2007/0041925 A1 | 2/2007 | Picano et al. | |

FOREIGN PATENT DOCUMENTS

| | | | |
|---|---|---|---|
| CN | 1475202 A | 2/2004 | |
| CN | 1531417 A | 9/2004 | |
| EP | 1 250 906 | 10/2002 | |
| EP | 1166762 | 10/2002 | |
| EP | 1166763 | 3/2003 | |
| EP | 1535607 | 6/2005 | |
| GB | 2 290 551 | 1/1996 | |
| GB | 2290551 | 1/1996 | |
| JP | 63301809 | * 12/1988 | ............... A61K 7/06 |
| JP | 4716632 B2 | 7/2011 | |
| WO | WO 90/03161 | 4/1990 | |
| WO | WO 02/072062 | 9/2002 | |
| WO | WO 2005/032505 | 4/2005 | |
| WO | WO 2006/045583 | 5/2006 | |
| WO | WO 2006/045584 | 5/2006 | |

OTHER PUBLICATIONS

Crotein Cashmere PE Technical Data Sheet DS-250R-1, Jun. 16, 2008.
Ceraphyl RMT Enableing Technology for Superior Moisturization from Wash-off Products, Ling Feng & Fu Yanhong, Detergent & Cosmetics, vol. 25, No. 3, p. 20-22 and 43, Jun. 2002 abstract.
Office Action from corresponding European application, Apr. 19, 2010.
Office Action from corresponding Chinese application, Feb. 12, 2010.
Translation of Examination Report from corresponding Korean application mailed on Feb. 25, 2010.
"Lipid Analogues—Ceraphyl RMT" from www.ispcorp.com. Retrieved on Aug. 8, 2006.
Osborne, D. "The Skin Softening Properties of Maleated Soybean Oil". Cosmetics and Toiletries. vol. 103. Aug. 1988.
Held, U. "L-Carnitine for your skin". Cosmoceuticals NOW. Spring 2004.
"Cola® Moist 200".—Product Information. Colonial Chemical, Inc., circa 2004.
"Ceraphyl® RMT".—Product Information. International Specialty Products, circa Apr. 2001.
International Search Report from PCT/US2008/082793 mailed on Jul. 8, 2009.
International Search Report and Written Opinion in International Application No. PCT/US06/033162, mailed Mar. 21, 2007.
Moore et al., 2006. "Maintaining Moisturization from Rinse-Off Products." Household & Personal Products Industry, pp. 77-81.

* cited by examiner

*Primary Examiner* — Benjamin Packard
(74) *Attorney, Agent, or Firm* — Michael F. Morgan

(57) ABSTRACT

A composition comprising: an adduct of a vegetable oil and maleic anhydride; and a material chosen from a hydrolyzed keratin, hydroxyethyl urea, and/or a quaternized nitrogen moisturizing agent.

9 Claims, No Drawings

MOISTURIZING COMPOSITIONS

CROSS REFERENCE TO RELATED APPLICATION

This application claims priority to U.S. Provisional Patent Application Ser. No. 60/711,121, filed on 25 Aug. 2005, which is incorporated herein by reference.

BACKGROUND OF THE INVENTION

Providing moisture to skin, hair, or nails has been the goal of many products to prevent dryness and/or promote moisturization. Some products have used materials as a barrier to prevent the moisture within the body from escaping. Other products use materials to attract moisture to the skin.

It would be desirable to provide a composition that could provide a desired level of moisture along with desired effects on skin, hair, and/or nails.

BRIEF SUMMARY OF THE INVENTION

A composition comprising: an adduct of a vegetable oil and maleic anhydride; and a material chosen from a hydrolyzed keratin, hydroxyethyl urea, and/or a quaternized nitrogen moisturizing agent. Also, a method of moisturizing skin, hair, and/or nails comprising applying an effective amount of the composition to skin, hair, and/or nails. Also, a method of depositing a substance to a substrate comprising applying the composition, which further comprises the substance, to a substrate.

DETAILED DESCRIPTION OF THE INVENTION

As used throughout, ranges are used as a shorthand for describing each and every value that is within the range. Any value within the range can be selected as the terminus of the range. The use of and/or indicates that any one from the list can be chosen individually, or any combination from the list can be chosen.

Unless indicated otherwise, the percentages specified herein are weight percentages based the active weight of the material in the total weight of the composition, which totals 100%.

The composition includes a vegetable oil maleate. The vegetable oil maleate is an adduct of a vegetable oil with maleic anhydride. The vegetable oil maleate can be present in the composition in any desired amount to give a desired level of moisturization. In one embodiment, the vegetable oil maleate is present in the composition at greater than 0 up to about 2% by weight. In another embodiment, the vegetable oil maleate is present at about 0.55% by weight.

A range of vegetable oils may be utilized for preparing the adduct with maleic anhydride including, for example, glycerin, in which the constituent hydroxyl groups are esterified with an equal or nearly equal number of fatty acid molecules. Many vegetable oils are triglycerides. i.e., those glycerides in which three fatty acid molecules are chemically bonded to the glycerin backbone. Vegetable oils suitable for use in the present invention include, but are not limited to, almond, arachis (peanut), avocado, castor, coconut, corn, cottonseed, crambie, jojoba, lesquerella (bladder-pod), linseed, olive, palm, rapeseed (canola), rice bran, persic (apricot kernal), safflower, sesame, soybean, sunflower and veronia.

Differences in the functional properties of vegetable oils are generally attributed to variations in their respective fatty acid constituents. Different fatty acids may be present in vegetable oils suitable for use in the invention including, for example, myristic, licanic, 12-hydroxyoleic, eleostearic, ricinoleic, palmitic, stearic, oleic, linoleic, linolenic, arachidic, eicosenoic, behenic, erucic, palmitiolic, docosadienoic, lignoseric, tetracossenoic, margaric, margaroleic, gadoleic, caprylic, capric, lauric, pentadecanioic, and heptadecanoic acids. These fatty acid molecules can also vary in their degree of unsaturation and their hydroxyl groups can react like typical secondary alcohols by being eliminated or esterified.

One example of a vegetable oil maleate is castoryl maleate, which may be prepared by reacting castor oil with maleic anhydride to form the adduct as described in U.S. Pat. No. 6,225,485, which is incorporated herein by reference. In one embodiment, the castoryl maleate does not contain free maleic anhydride. The castoryl maleate adduct may be manufactured by reacting castor oil and cyclic carboxylic acid anhydride at a temperature of 75-120° C. for an initial period of, for example, 4 to 24 hours, and then continuing the reaction at room temperature for at least one week to ensure that substantially all of the maleic anhydride has been reacted.

In addition to the vegetable oil maleate, the composition includes a moisturizing agent chosen from a hydrolyzed keratin, hydroxyethyl urea, and/or a quaternized nitrogen moisturizing agent. Any one of these can be used alone, or any combination of these materials can be used.

In one embodiment, a hydrolyzed keratin is present in the composition. Any hydrolyzed keratin can be included in the composition. In one embodiment, the hydrolyzed keratin comprises an extract of goat hair. In one embodiment, the goat hair is cashmere. The hydrolyzed keratin can be present in the composition in any desired amount to give a desired level of moisturization. In one embodiment, the hydrolyzed keratin is present in an amount of 0 to about 0.005% by weight. In another embodiment, the hydrolyzed keratin is present in an amount of about 0.0005 to about 0.005% by weight. In another embodiment, the hydrolyzed keratin is present at about 0.0015% by weight.

In one embodiment, hydroxyethyl urea is present in the composition. The hydroxyethyl urea can be present in the composition in any desired amount to give a desired level of moisturization. In one embodiment, the hydroxyethyl urea is present in an amount of 0 to about 13% by weight. In one embodiment, the hydroxyethyl urea is present at about 6% by weight.

In one embodiment, a quaternary nitrogen moisturizing agent is present in the composition. The quaternary nitrogen moisturizing agent is a moisturizing agent that contains a quaternary nitrogen in its structure. Examples of quaternary nitrogen moisturizing agents include, but are not limited to, hydroxypropyl bis-hydroxyethyldimonium chloride (available as COLA™ Moist 200 from Colonial Chemicals, Inc.) having the structure

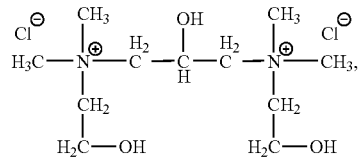

a material having the structure

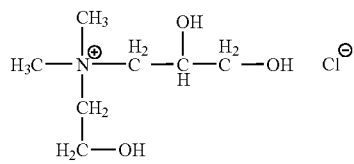

(which is described in U.S. Pat. No. 6,869,977, a choline salt (which is described in U.S. Pat. Nos. 6,475,965 and 6,265,364, both of which are incorporated herein by reference), carnitine, and combinations thereof. Naturally occurring carnitine is L-carnitine. The quaternary nitrogen moisturizing agent can be present in the composition in any desired amount to give a desired level of moisturization. In one embodiment, the quaternary nitrogen moisturizing agent is present in an amount of 0 to about 5. In another embodiment, the quaternary nitrogen moisturizing agent is present in an amount of about 0.1 to about 1% by weight. In another embodiment, the quaternary nitrogen moisturizing agent is present at about 1% by weight.

Additionally, glycerin may be included in the composition in combination with the moisturizing agent. The glycerin can be included in any desired amount to provide a desired level of moisturization. In one embodiment, the glycerin is present in an amount of 0 to about 8% by weight. In other embodiments, the glycerin can be present at about 6% by weight or about 1.5% by weight.

The composition may also contain creatine. Creatine can be used to support the energy cycle in skin cells. Creatine can be included at any desired amount to achieve any desired level of energy support in cells. In one embodiment, the creatine is present in the composition in an amount of 0 to about 2% by weight.

The cleansing compositions may also include one or more anionic surfactants, amphoteric surfactants, nonionic surfactants, cationic surfactants, and combinations thereof. Those of ordinary skill in the art will be aware of suitable surfactants and other additives readily identifiable from the *International Cosmetic Ingredient Dictionary and Handbook*, 10$^{th}$ ed., (2004). Surfactants can be included in any desired amount. In one embodiment, surfactants are present in the composition in an amount of 0 to about 40% by weight. In one embodiment, the surfactants are present in an amount of about 1 to about 40% by weight. In one embodiment, surfactants are present in the composition in an amount of about 5 to about 40% by weight. In one embodiment, the surfactants are present in an amount of about 1 to about 10% by weight.

A variety of anionic surfactants can be utilized in the moisturizing body wash composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount. In one embodiment, anionic surfactants are present in the composition in an amount of 0 to about 15% by weight. In one embodiment, anionic surfactants are present in an amount of about 6 to about 8% by weight.

Amphoteric surfactants may also be included in the composition. These surfactants are typically characterized by a combination of high surfactant activity, lather forming and mildness. Amphoteric surfactants include, but are not limited to derivatives of aliphatic secondary and tertiary amines in which the aliphatic radical can be straight chain or branched and wherein one of the aliphatic substituents contains about 8 to about 18 carbon atoms and one contains an anionic water solubilizing group. e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines. Amphoteric surfactants can be included in any desired amount. In one embodiment, amphoteric surfactants are present in the composition in an amount of 0 to about 15% by weight. In one embodiment, the amphoteric surfactants are present in an amount of about 4 to about 6% by weight.

Examples of nonionic surfactants include, but are not limited to, polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof. Nonionic surfactants can be included in any desired amount. In one embodiment, nonionic surfactants are present in the composition in an amount of 0 to about 3% by weight. In one embodiment, nonionic surfactants are present in the composition in an amount of about 0.5 to about 1.5% by weight.

Cationic surfactants can also be included in the composition. Examples of cationic surfactants include, but are not limited to any quaternium or polyquaternium compound. Cationic surfactants can be included at any desired level. In one embodiment, cationic surfactants are present in the composition in an amount of 0 to about 2% by weight. In one embodiment, cationic surfactants are present in the composition in an amount of about 0.1 to about 0.3% by weight.

Many additional surfactants are described in McCUTCHEON'S DETERGENTS AND EMULSIFIERS (1989) and other reference materials that are well known to those of ordinary skill in the art.

Skin compatible oils can be included in the composition. Skin compatible oils include a range of liquid hydrocarbons, for example, linear and branched oils such as liquid paraffin, squalene, squalane, mineral oil, low viscosity synthetic hydrocarbons such as polyalphaolefins, commercially available from ExxonMobil under the trade name PURESYN PAO and polybutene under the trade name PANALANE™ or INDOPOL™. Light (low viscosity) highly branched hydrocarbon oils may also be suitable in some instances. Other useful skin compatible oils may be silicone based, for example, linear and cyclic polydimethyl siloxane, organo functional silicones (alkyl and alkyl aryl), and amino silicones.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents (0 to 3% by weight); glyceryl esters and derivatives, for example glycol distearate, and/or their equivalents (0 to 3%; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); stabilizers, for example, metal salts of fatty acids, such as e.g. magnesium stearate, aluminum stearate and/or zinc stearate (0 to 2% by a weight); and dyes and pigments that are approved and suitable for cosmetic purposes.

Water may be included in the composition. Water can be included in an amount of 0 to about 90% by weight. In one embodiment, water is present at about 50% to about 90% by weight.

In one embodiment, a moisturizing body wash composition also utilizes, as a thickening agent, a blend of PEG-150 distearate and PPG-2 hydroxyethyl cocamide for countering a decrease in viscosity associated with the concentrations of moisturizing agents utilized in some embodiments of the moisturizing body wash composition. This blended thickening agent allows the composition to achieve viscosities beyond those that could be achieved with conventional thickening agents, for example sodium chloride alone, and is able to achieve suitable viscosities at relatively low concentrations. The relatively low concentrations used to achieve the desired viscosities are also advantageous with respect to manufacturing processes that may be employed to manufacture the moisturizing body wash composition, thereby reducing the need for larger equipment or modifications and the capital expenditure associated with manufacturing the moisturizing body wash composition if other thickening agents were used. The PEG-150 distearate and the PPG-2 hydroxyethyl cocamide can be present in any amount to achieve a desired viscosity. In one embodiment, the amount of PEG-150 distearate in the composition is 0 to about 2% by weight.

In one embodiment, the amount of PPG-2 hydroxyethyl cocamide in the composition is 0 to about 2% by weight. In one embodiment, the weight ratio of the PEG-150 distearate to the PPG-2 hydroxyethyl cocamide can be about 3:1 to about 1:3. In one embodiment the PEG-150 distearate and the PPG-2 hydroxyethyl cocamide are each present at 0.0225% by weight. The PEG-150 distearate and the PPG-2 hydroxyethyl cocamide are available as a mixture from Uniqema under the trade name PROMIDIUM™ LTS.

The composition can be used to moisturize skin, hair, and/or nails. The composition is applied to skin, hair, and/or nails. If the composition is a rinse off composition, the composition is rinsed off. The composition can be left on for any desired amount of time. The composition can be included in any product that contacts skin, including the oral cavity hair, and/or nails. The composition can be used on humans or other animals. The composition can be in the form of a body wash, a shower gel, a hand wash, a soap bar, a shampoo, a conditioner, a dishwashing liquid, a skin lotion, a sunscreen, a bubble bath, an oral care product, a dentifrice, a toothpaste, a mouthwash, an antiperspirant, a deodorant, or a foot soak.

The composition can also be used to apply a substance to a substrate. The substance is included in the composition, and the composition is applied to a substrate. The substrate can be any desired substrate. In one embodiment, the substrate can be skin, hair, and/or nails. The substance can be any substance that is attracted to the composition. In one embodiment, the substance is chosen from fragrances, sunscreen, pigments, insect repellents, and/or hydrophobic materials.

The following examples are merely illustrative and do not in any way limit the scope of the invention as described and claimed. Unless otherwise listed, the amount are % by weight of the composition based on the active weight of the material.

Example 1

A moisturizing body wash composition can be prepared that includes hydrolyzed cashmere. The formulation of this moisturizing body wash composition is provided below in Table 1. The base used in this and other examples is shown in Table 2.

TABLE 1

| Phase | Ingredient | % Wt. Range |
|---|---|---|
| PHASE A | Base | 70-85 |
| PHASE B | Castoryl Maleate | 0.1-2 |
| | Glycerin | 1-8 |
| | Extract of cashmere goat hair | 0.0005-0.005 |
| | Cocamidopropyl Betaine | 1-15 |
| PHASE C | Fragrance | 0.1-3 |
| | Citric Acid Solution | 0.001-0.2 |
| | Sodium Chloride | 1-5 |
| Total | | 100 |

TABLE 2

| Base | |
|---|---|
| Ingredient Name | % Wt. Range |
| Demineralized Water | 84-87 |
| DMDM Hydantoin | 0.2-0.4 |
| Polyquaternium-7 | 0.15-0.25 |
| $SO_3Na$ Pareth 145-2EO Sulfate | 8-10 |
| Cocamidopropyl Betaine | 2.5-4 |
| Decyl Glucoside | 1-2 |

TABLE 2-continued

| Base | |
|---|---|
| Ingredient Name | % Wt. Range |
| Ethylene Diamine Tetra Acetic Acid (EDTA) | 0.05-1 |
| Total Materials | 100 |

Example 2

A moisturizing body wash composition can be prepared that includes a hydroxyethyl urea (for example HYDROVANCE™, commercially available from National Starch and Chemical, Bridgewater, N.J.). The formulation of this moisturizing body wash composition is provided below in Table 3.

TABLE 3

| Phase | Ingredient | % Wt./Wt. | % Wt. Range |
|---|---|---|---|
| PHASE A | Base | 82.31 | 70-85 |
| PHASE B | Castoryl Maleate | 0.55 | 0.1-2 |
| | Hydroxyethyl urea | 6 | 1-13 |
| | Cocamidopropyl Betaine | 8 | 1-15 |
| PHASE C | Fragrance | 1.1 | 0.1-3 |
| | Citric Acid Solution | 0.04 | 0.001-0.2 |
| | Sodium Chloride | 2 | 1-5 |
| Total | | 100 | 100 |

Example 3

A composition containing a blend of glycerin and hydroxyethyl urea can also be prepared as shown below in Table 4.

TABLE 4

| Phase. | Ingredient | % Wt./Wt. | % Wt. Range |
|---|---|---|---|
| PHASE A | Base | 78.71 | 70-85 |
| PHASE B | Castoryl Maleate | 0.55 | 0.1-2 |
| | Glycerin | 3 | 0.1-6 |
| | Hydroxyethyl urea | 3 | 0.1-6 |
| | Cocamidopropyl Betaine | 8 | 1-15 |
| PHASE C | Ethylene glycol distearate | 3.5 | 0.5-7 |
| | DMDM Hydantoin | 0.1 | 0.01-0.2 |
| PHASE D | Fragrance | 1.1 | 0.1-3 |
| | Citric Acid Solution | 0.04 | 0.005-0.1 |
| | Sodium Chloride | 2 | 0.1-5 |
| Total | | 100 | 100 |

Example 4

In another example, the 6% hydroxyethyl urea in the formula in Table 3 can be replaced with 1% by weight hydroxypropyl bis-hydroxyethyldimonium chloride (COLA™ Moist 200) and 1.5% by weight glycerin. All materials, except water, remain at the same amount. The amount of water is adjusted to provide for 100% by weight.

The moisturizing body wash compositions having the representative formulation described above can be manufactured by combining the components identified in Table 2 to prepare a base. This base is, in turn, used as Phase A in the moisturizing body wash composition. The Phase B components are then combined and well mixed to form Phase B. Phase B is then added into Phase A with mixing to form an intermediate composition. If desired, fragrance and colorants may be added to the intermediate composition and mixed until the mixture is clear. The Phase C components may then be added as necessary and mixed to obtain a substantially uniform composition. The pH and viscosity of the composition may then be adjusted as needed to produce a final composition having a viscosity of about 12,000 to about 15,000 cPs (as measured with a Brookfield DV-II Viscometer No. 5 Spindle at 20 rpm at 25° C.) and a slightly acidic pH of about 5 to about 6.

Various modifications of the invention, in addition to those described herein, will be apparent to those skilled in the art from the foregoing description. Such modifications are also intended to fall within the scope of the appended claims.

What is claimed is:

1. A composition comprising:
   about 0.1 to about 2% by weight castor oil maleate
   about 0.0005 to about 0.005% by weight hydrolyzed keratin from goat hair,
   an alkyl ether sulfate surfactant,
   cocamidopropyl betaine surfactant, and
   about 1 to about 8 weight % glycerin.

2. The composition of claim 1 further comprising creatine.

3. The composition of claim 1 further comprising PEG 150 distearate and PPG-2 hydroxyethyl cocamide.

4. A method of moisturizing skin, hair, and/or nails comprising applying an effective amount of the composition of claim 1 to skin, hair, and/or nails.

5. The method of claim 4 further comprising rinsing the composition from the skin, hair, and/or nails.

6. A method of depositing a substance to a substrate comprising applying the composition of claim 1, which further comprises the substance, to a substrate.

7. The method of claim 6, wherein the substance is chosen from fragrances, sunscreen, pigments, insect repellents, and/or hydrophobic materials.

8. The composition of claim 1, wherein
   the castor oil maleate is present at about 0.55% by weight, and
   the hydrolyzed keratin from goat hair is present at about 0.0015% by weight.

9. The composition of claim 1 comprising:
   about 0.55% by weight of the castor oil maleate,
   about 0.0015% by weight of the hydrolyzed keratin from goat hair,
   about 8 to about 10% by weight of the alkyl ether sulfate surfactant,
   about 4 to about 6% by weight of the cocamidopropyl betaine surfactant, and
   about 6% by weight glycerin.

* * * * *